United States Patent
Kawamoto et al.

(10) Patent No.: US 12,194,083 B2
(45) Date of Patent: Jan. 14, 2025

(54) METHOD FOR ESTABLISHING PLURIPOTENT STEM CELLS BEARING GENES ENCODING ANTIGEN SPECIFIC T CELL RECEPTOR

(71) Applicant: Hiroshi Kawamoto, Kyoto (JP)

(72) Inventors: Hiroshi Kawamoto, Kyoto (JP); Kyoko Masuda, Kyoto (JP); Takuya Maeda, Kyoto (JP); Yoshimoto Katsura, Abiko (JP)

(73) Assignee: Hiroshi Kawamoto, Kyoto (JP)

( * ) Notice: Subject to any disclaimer, the term of this patent is extended or adjusted under 35 U.S.C. 154(b) by 699 days.

(21) Appl. No.: 15/326,973

(22) PCT Filed: Jul. 17, 2015

(86) PCT No.: PCT/JP2015/070623
§ 371 (c)(1),
(2) Date: Jun. 19, 2017

(87) PCT Pub. No.: WO2016/010154
PCT Pub. Date: Jan. 21, 2016

(65) Prior Publication Data
US 2017/0304417 A1    Oct. 26, 2017

Related U.S. Application Data

(60) Provisional application No. 62/026,336, filed on Jul. 18, 2014.

(51) Int. Cl.
| | |
|---|---|
| *A61K 39/00* | (2006.01) |
| *A61K 35/17* | (2015.01) |
| *C07K 14/725* | (2006.01) |
| *C12N 5/074* | (2010.01) |
| *C12N 5/0783* | (2010.01) |
| *C12N 15/09* | (2006.01) |

(52) U.S. Cl.
CPC .......... *A61K 39/0011* (2013.01); *A61K 35/17* (2013.01); *C07K 14/7051* (2013.01); *C12N 5/0638* (2013.01); *C12N 5/0696* (2013.01); *C12N 15/09* (2013.01); *A61K 2039/5156* (2013.01); *A61K 2039/572* (2013.01); *C12N 2506/45* (2013.01); *C12N 2510/00* (2013.01)

(58) Field of Classification Search
CPC ............... A61K 39/0011; A61K 35/17; A61K 2039/5156; A61K 2039/572; C12N 15/09; C12N 5/0638; C12N 5/0696; C12N 2506/45; C12N 2510/00; C07K 14/7051
See application file for complete search history.

(56) References Cited

U.S. PATENT DOCUMENTS

| | | | |
|---|---|---|---|
| 2003/0039635 A1* | 2/2003 | Gaiger | C07K 14/4748 424/93.2 |
| 2009/0217403 A1 | 8/2009 | Spits | |
| 2011/0020932 A1 | 1/2011 | Hiroshi et al. | |
| 2013/0078226 A1* | 3/2013 | Nakauchi | A61K 39/21 424/93.71 |

FOREIGN PATENT DOCUMENTS

| | | | | |
|---|---|---|---|---|
| GB | 2484869 A | 4/2012 | | |
| JP | 2006-306822 A | 11/2006 | | |
| WO | 2008038579 A | 4/2008 | | |
| WO | 2011021503 A | 2/2011 | | |
| WO | WO-2011068962 A1 * | 6/2011 | ........... | C12N 5/0636 |
| WO | 2011096482 A | 8/2011 | | |
| WO | WO-2014165707 A2 * | 10/2014 | ..... | A61K 39/001193 |

OTHER PUBLICATIONS

Ochi et al., Tumor Immunotherapy Poster II Nov. 20, 2009, Development of Novel Stem Cell Transplantation and Gene-Immunotherapy Using WT1-Specific T-Cell Receptor Gene. Abstract 3028 Poster Board II-1004 American Society of Hematology (Year: 2009).*
Vizcardo et al., Regeneration of Human Tumor Antigen Specific T cells from iPSCs Derived from Mature CD8+ T Cells. Cell Stem Cell 12, 31-36 Jan. 3, 2013. (Year: 2013).*
Vizcardo et al. Regeneration of Human Tumor Antigen Specific T cells from iPSC derived from mature CD8+ Tcells. Cell Stem Cell. 12, 31-36 Jan. 3, 2013 (Year: 2013).*
Snauwaert et al.In vitro generation of mature, naive antigen-specific CD8b T cells with a single T-cell receptor by agonist selection. Leukemia 28, 830-841. advance online publication, Oct. 25, 2013 (Year: 2013).*
Lei et al. Dual signals of TCR and Notch promote antigen-specific T cell development from pluripotent stem cells (P4370).J Immunol May 1, 2013, 190 (1 Supplement) 177.18. Of record. (Year: 2013).*
Minagawa et al. Production of Antigen-Specific T Cells From iPS Cells Using Genome Editing. 18th Meeting of the Japan Association of Cancer Immunology. Translation. Original copy of record. (Year: 2014).*

(Continued)

Primary Examiner — Amy E Juedes
Assistant Examiner — Brian Hartnett
(74) *Attorney, Agent, or Firm* — LATHROP GPM LLP; James H. Velema, Esq.; Judith Stone-Hulslander (57) ABSTRACT

Provided is a method for inducing T cells for a cell-based immunotherapy, comprising the steps of:
(1) providing human pluripotent stem cells bearing genes encoding a T cell receptor specific for a desired antigen, and
(2) inducing T cells from the pluripotent stem cells of step (1). The human pluripotent stem cells bearing genes encoding the desired antigen specific T cell receptor may be prepared by introducing genes encoding the desired antigen specific T cell receptor into pluripotent stem cells.

8 Claims, 7 Drawing Sheets
Specification includes a Sequence Listing.

(56) References Cited

OTHER PUBLICATIONS

WT1-specific T cell receptor gene therapy: Improving TCR function in transduced T cells. Stauss et al. Blood Cells, Molecules, and Diseases 40 (2008) 113-116 (Year: 2008).*
Jurgens et al. (2006) "Transduction of primary lymphocytes with Epstein-Barr virus (EBV) latent membrane protein-specific T-cell receptor induces lysis of virus-infected cells: A novel strategy for the treatment of Hodgkin's disease and hasopharyngeal carcinoma," J. Clin. Immunol. 26(1):22-32.
Lei et al. (2011) "In Vivo Programming of Tumor Antigen-Specific T Lymphocytes from Pluripotent Stem Cells to Promote Cancer Immunosurveillance," Cancer Res. 71(14):4742-4747.
Lei et al. (May 2013) "Dual signals of TCR and Notch promote antigen-specific T cell development from pluripotent stem cells (P4370)," In; The Meeting Abstracts of Immunology, May 3-7, 2013. Honolulu, Hawaii. J. Immunol. 190(1 Suppl):177.18.
Riolobos et al. (Apr. 30, 2013) "HLA engineering of human pluripotent stem cells," Mol. Ther. 21(6):1232-1241.
Tamanaka et al. (Dec. 2012) "Recognition of a Natural WT1 Epitope by a Modified WT1 Peptide-specific T-Cell Receptor," Anticancer Res. 32(12):5201-5210.
Themeli et al. (Aug. 11, 2013) "Generation of tumor-targeted human T lymphocytes from induced pluripotent stem cells for cancer therapy," Nat. Biotechnol. 31(10):928-933.
International Search Report with Written Opinion corresponding to International Patent Application No. PCT/JP2015/070623, mailed Aug. 25, 2015.
Hiroshi Kawamoto et al., Regenerative Medicine, Jan. 2014, vol. 13, supplement 2014, p. 176, SY-25-4.
Horishi Kawamoto et al., The 18th General Meeting of Japanese Association of Cancer Immunology Program/Proceedings, Jun. 2014, p. 50, S1-3.
Watarai et al. (2010) "Generation of functional NKT cells in vitro from embryonic stem cells bearing rearranged invariant Va14-Ja TCRa gene," Blood, 15(2), 9 pages.
Vizcardo et al. (2013) "Regeneration of Human Tumor Antigen-Specific T cells from iPSCs Derived from Mature CD8+ T cells," Cell Stem Cell, 12:31-36.
Nishimura et al. (2013) "Generation of Rejuvenated Antigen-Specific T Cells by Reprogramming to Pluripotency and Redifferentiation," Cell Stem Cell, 12:114-126.
Morgan et al. (2006) "Cancer Regression in Patients After Transfer of Genetically Engineered Lymphocytes," Science, 314(5796), 10 pages.
Okamoto et al. (2009) "Improved Expression and Reactivity of Transduced Tumor-Specific TCRs in Human Lymphocytes by Specific Silencing of Endogenous TCR," Cancer Research, 69(23):9003-9011.
Chapuis et al. (2013) "Transferred WT1-reactive CD8+ T cells can mediate antileukemic activity and persist in post-transplant patients," Sci. Transl. Med., 5(174), 25 pages.
Barker et al. (2010) "Successful treatment of EBV-associated post-transplantation lymphoma after cord blood transplantation using third-party EBV-specific cytotoxic T lymphocytes," Blood, 116(23):5045-5049.
Takahashi et al. (2006) "Induction of Pluripotent Stem Cells from Mouse Embryonic and Adult Fibroblast Cultures by Defined Factors," Cell, 126:663-676.
Takahashi et al. (2007) "Induction of Pluripotent Stem Cells from Adult Human Fibroblasts by Defined Factors," Cell, 131:861-872.
Grskovic et al. (2011) "Induced pluripotent stem cells—opportunities for disease modelling and drug discovery," Nature Reviews Drug Discovery, 10:915-929.
Timmermans et al. (2009) "Generation of T Cells from Human Embryonic Stem Cell-Derived Hematopoietic Zones," The Journal of Immunology, pp. 6879-6888.
Ito et al. (1988) "Change of HLA Phenotype in Postoperative Erythroderma," The Lancet, pp. 413-414.
Cyranoski et al. (2012) "Stem-cell pioneer banks on future therapies," Nature, 488, p. 439.
Doulatov et al. (2010) "Revised map of the human progenitor hierarchy shows the origin of macrophages and dendritic cells in early lymphoid development," Nature Immunology, 11(7):585-595.
Hao et al. (2008) "Human intrathymic lineage commitment is marked by differential CD7 expression: identification of CD7-lympho-myeloid thymic progenitors," Blood, 111(3):1318-1326.
Ohminami et al. (2000) "HLA class I-restricted lysis of leukemia cells by a CD8+ cytotoxic T-lymphocyte clone specific for WT1 peptide," Blood, 95(1):286-293.
Ochi et al. (2011) "Novel adoptive T-cell immunotherapy using a WT1-specific TCR vector encoding silencers for endogenous TCRs shows marked antileukemia reactivity and safety," Blood, 118(6):1495-1503.
Fujiki et al. (2008) "A WT1 protein-derived, naturally processed 16-mer peptide, WT1 332, is a promiscuous helper peptide for induction of WT1-specific TH1-type CD4+ T cells," Microbiol Immunol, 52:591-600.
Oka et al. (2000) "Cancer Immunotherapy Targeting Wilms' Tumor Gene WT1 Product," The Journal of Immunology, The American Association of Immunologists, US, 164(15):1873-1880.
May et al. (2007) "Peptide Epitopes from the Wilms' Tumor1 Oncoprotein Stimulate CD4+ and CD8+ T Cells That Recognize and Kill Human Malignant Mesothelioma Tumor Cells," Clinical Cancer Research, 13(15):4547-4555.
Extended European Search Report corresponding to European Patent Application No. 15822874.2, dated Feb. 21, 2018.
English translation of the International Preliminary Report on Patentability corresponding to International Application No. PCT/JP2015/070623, issued Jan. 24, 2017.
Hiroshi Kawamoto, (2013), Clinical Oncology, 12(4):450-459.
Minagawa Atsutaka et al. (2014), Hermatology Frontier, 24(2):39-45.
Hiroshi Kawamoto, (2014) "Regeneration of antigen specific T cells using the iPSC technology: A novel strategy for cancer immunotherapy," Regenerative Medicine, 13, 3 pages.
Takuya Maeda et al. (2014) Regenerative Medicine, 13, Supplement 2014, p. 226.
Minagawa Atsutaka et al.(2014), The 18th General Meeting of Japanese Association of Cancer Immunology Program/Proceedings, p. 161.
Minagawa et al., "Rise of iPSCs as a cell source for adoptive immunotherapy", Human Cell, Apr. 2014, 27(2): 47-50.
O'Reilly et al., "Adoptive transfer of unselected or leukemia-reactive T-cells in the treatment of relapse following allogenic hematopoietic cell transplantation", Seminars in Immunology, 2010, 22: 162-172.
Vatakis et al., "Introduction of Exogenous T-cell Receptors Into Human Hematopoietic Progenitors Results in Exclusion of Endogenous T-cell Receptor Expression", Molecular Therapy, May 2013, 21(5): 1055-1063.
Ochi, Toshiki et al. (Nov. 2009) "Development of Novel Stem Cell Transplantation and Gene-Immunotherapy Using WT1-Specific T-Cell Receptor Gene," Blood, vol. 114(22): 3029.

\* cited by examiner

Figure 5 phase-contrast microscopy fluorescence microscopy

SEQUENCE LISTING

```
<160> NUMBER OF SEQ ID NOS: 6

<210> SEQ ID NO 1
<211> LENGTH: 28
<212> TYPE: DNA
<213> ORGANISM: Artificial
<220> FEATURE:
<223> OTHER INFORMATION: Primer for PCR

<400> SEQUENCE: 1
cacaggctgt cttacaatct tgcagatc                                      28

<210> SEQ ID NO 2
<211> LENGTH: 23
<212> TYPE: DNA
<213> ORGANISM: Artificial
<220> FEATURE:
<223> OTHER INFORMATION: Primer for PCR

<400> SEQUENCE: 2
ctccacttcc agggctgcct tca                                           23

<210> SEQ ID NO 3
<211> LENGTH: 24
<212> TYPE: DNA
<213> ORGANISM: Artificial Sequence
<220> FEATURE:
<223> OTHER INFORMATION: Primer for PCR

<400> SEQUENCE: 3
tgacctggga tggttttgga gcta                                          24

<210> SEQ ID NO 4
<211> LENGTH: 9
<212> TYPE: PRT
<213> ORGANISM: Homo sapiens

<400> SEQUENCE: 4
```

```
Cys Met Thr Trp Asn Gln Met Asn Leu
1               5

<210> SEQ ID NO 5
<211> LENGTH: 9
<212> TYPE: PRT
<213> ORGANISM: Homo sapiens

<400> SEQUENCE: 5

Arg Met Phe Pro Asn Ala Pro Tyr Leu
1               5

<210> SEQ ID NO 6
<211> LENGTH: 16
<212> TYPE: PRT
<213> ORGANISM: Homo sapiens

<400> SEQUENCE: 6

Lys Arg Tyr Phe Lys Leu Ser His Leu Gln Met His Ser Arg Lys His
1               5                   10                  15
```

METHOD FOR ESTABLISHING PLURIPOTENT STEM CELLS BEARING GENES ENCODING ANTIGEN SPECIFIC T CELL RECEPTOR

RELATED APPLICATIONS

This application is a 35 U.S.C. § 371 filing of International Application No. PCT/JP2015/070623, filed Jul. 17, 2015, which claims priority to U.S. Patent Application No. 62/026,336, filed Jul. 18, 2014. The content of each of these applications is incorporated herein by reference in its entirety.

The present application relates to a cell-based immunotherapy. Specifically, a method for preparing cells to be used for the cell-based immunotherapy by introducing genes encoding a T cell receptor specific for a desired antigen into pluripotent stem cells.

BACKGROUND ART

Each T cell expresses a T cell receptor (TCR) with different specificity. When an infectious disease develops, a T cell having a suitable specificity will proliferate to give a T cell population (clone) that will fight with the pathogen. This is the basic idea of the acquired immunity. If it is possible to artificially amplify a T cell with a desired specificity, the amplified T cells may be used for the adoptive immunotherapy. The amplification of a given T cell is called as "cloning". In fact, autologous transplantation of antigen specific T cells prepared by amplifying the antigen specific T cell obtained from the patient has been clinically conducted. However, almost all autologous T cell transplantation therapies do not use a cell population purified to the extent of "cloned" cells. In addition, repeated in vitro sub-culturing of the cells might cause loss of the function to kill the cancer cells.

A method for providing T cells that are capable of infinitely proliferating by immortalizing the cells has been proposed. A cell may be immortalized and proliferated to give a cloned cell population. Procedures to immortalize a cell may include fusion of the cell with a cancer cell as well as long term culture of the cells with stimulating TCR under the presence of cytokines. However, auto-transplantation of thus obtained immortalized T cells may be dangerous because the cells are cancer cells. In addition, the cloning procedures could lower the cell function.

Cell-based immunotherapies in which T cells are transplanted proposed up to now are briefly explained below.

A. Cloning of T cells Utilizing the Reprogramming Technique

Methods in which stem cells bearing genes encoding an antigen specific TCR are clonally expanded by using the reprogramming technique have been proposed. This method is expected to dissolve the problems in autologous transplantation of T cells. Specifically, pluripotent stem cells are generated from T cells by means of nuclear transplantation or the technique for establishing iPS cells. Patent applications directing to this concept have been submitted (WO2008/038579 and WO2011/096482). Papers on those methods have been published in 2010 and 2013:

1) Watarai H, A Rybouchkin, N Hongo, Y Nagata, S Sakata, E Sekine, N Dashtsoodol, T Tashiro, S-I Fujii, K Shimizu, K Mori, K. Masuda, H Kawamoto, H Koseki, and M Taniguchi. Generation of functional NKT cells in vitro from embryonic stem cells bearing rearranged invariant Vα14-Jα18 TCRα gene. Blood.115:230-237.2010.

2) Vizcardo R, Masuda K, Yamada D, Ikawa T, Shimizu K, Fujii S-I, Koseki H, Kawamoto H. Regeneration of human tumor antigen-specific T cells from iPS cells derived from mature CD8+ T cells. Cell Stem Cell. 12: 31-36. 2013.

3) Nishimura T et al.Cell Stem Cell.12: 114-226. 2013.

In those methods, ES cells or iPS cells are established from the patient's T cells, T cells are reproduced from those ES or iPS cells and then, the regenerated T cells are transplanted to the patient (autologous transplantation). However, the methods have at least three problems shown below: A1) iPS cells must be established from each patient and therefore, previous preparation for the therapy applicable for various people is impossible; A2) iPS cells are established for each patient and therefore, the quality and safety of the obtained iPS cells may vary each time; and A3) T cells differentiated from the T-iPS cells may become cancer.

B. T Cell Therapy in Which T Cells Introduced with Genes Encoding a TCR are Used Clinical test for gene therapies in which genes encoding an antigen specific T cell receptor (TCR) are isolated and the genes are transfected in the normal T cells obtained from the patient to be treated, the transfected T cells are then transplanted to the patient (autologous transplantation) have been conducted in various places (Morgan R. A. et al.Science.314:126.2006). The T cells are obtained as aggregate of various clones. According to this method, expression of the TCR originally present in the normal T cells is suppressed by, for example, siRNA (Okamoto S et al, Cancer Res 69:9003, 2009). Thus obtained T cells expressing only the specific TCR are subjected to the autologous transplantation. For example, genes encoding a T cell receptor specific for a WT1 antigen have been isolated. Gene therapy using the TCR genes for treating WT1 expressing cancers has been conducted.

In the method B, T cells used for the therapy are also prepared from the T cells of the patient to be treated. This method has three problems as follows. B1) There is a risk that the patient's T cells become cancer, because this is a gene therapy; B2) The expression of endogenous genes encoding the original TCR in the T cells to be transplanted may not perfectly be suppressed and therefore, there is a risk of unintended reaction; B3) T cells must be prepared from each patient and therefore, previous preparation for the therapy applicable for various people is impossible C. Donor Lymphocyte Infusion Bone marrow transplantation for hematological malignancy such as leukemia also has an aspect as a cell-based immunotherapy. That is, T cells contained in the transplanted bone marrow cells of the donor are expected to attack against the leukemia cells in the recipient. Donor lymphocyte infusion, in which donor's T cells are separately infused after the bone marrow transplantation in order to enhance the effect, has also been known. Recently, a new method in which clonally expanded T cells specific for a given antigen are infused has been proposed (Chapuis et al. Sci Transl Med. 5:174ra27.2013).

In this method, the T cells to be infused are derived from a donor. However, the hematopoietic system of the recipient after receiving the bone marrow transplantation has become the same as that of the donor. Accordingly, the T cell infusion after the bone marrow transplantation is deemed as a sort of autologous transplantation. This method requires bone marrow transplantation and the patient needs to receive immunosuppressant for his/her entire life.

D. Use of Umbilical Code Lymphocyte for Treating Another Person

Patients who received umbilical cord blood transplantation sometimes develop a viral infectious disease due to the lowered immunizing capacity. In order to treat said patients, infusion of viral specific CTLs contained in umbilical cord blood derived from a person other than the person from whom the original umbilical cord was obtained has been proposed (Blood.116:5045.2010). A patent application on an idea of transplanting CTLs of a donor having HLAs that match the patient's HLAs to the some extent but not completely has been submitted (WO2011/021503). However, T cells in the umbilical cord blood are aggregate of clones, i.e. an aggregate of the cells bearing a number of different TCRs. Therefore, cannot perfectly avoid a risk of exerting graft-versus-host disease (GVHD).

As discussed above, a variety of cell-based immunotherapies using T cells have been proposed. All therapies except D are autologous cell transplantation or are deemed to be autologous transplantation. Heterologous T cell transplantation is contrary to the common general technical knowledge. In the treatment of hematological malignancy such as leukemia, for example, bone marrow transplantation in which hematopoietic stem cells is, in general, conducted. In order to avoid the rejection of the donor's bone marrow by the recipient, bone marrow from a donor who has HLAs that match the recipient's HLAs is used.

However, amino acid sequences of various proteins other than HLAs do not match between two people and donor's T cells may recognize those mismatches as targets for attack. As a result, a part of the transplanted donor's T cells attack against the recipient's body, i.e. graft-versus-host reaction could exert, and put the recipient to die (Ito et al Lancet, 331: 413, 1988).

A project to create a highly versatile iPS cell bank with donors having HLA haplotypes that are frequently found in Japanese people in homozygous is in progress. (CURANOSKI.Nature vol.488.139.2012). However, in T cell transplantation, even if the donor has HLAs that completely match the recipient's HLAs, there is still a risk of graft-versus-host reaction. Further, when HLAs mismatch, more severe graft-versus-host reaction is expected. Accordingly, this iPS stock project has been inapplicable for the cell-based immunotherapy that uses T cells.

PRIOR ART DOCUMENTS

Patent Documents

[Patent Literature 1] WO2008/038579
[Patent Literature 2] WO2011/096482
[Patent Literature 3] WO02011/021503

Non Patent Document

[Non-Patent Literature 1] Watarai et al. Blood.115:230-237.2010.
[Non-Patent Literature 2] Vizcardo et al. Cell Stem Cell.12: 31-36.2013.
[Non-Patent Literature 3] Nishimura T et al. Cell Stem Cell.12:114-226.2013.
[Non-Patent Literature 4] Morgan R. A. et al.Science. 314: 126.2006
[Non-Patent Literature 5] Okamoto S et al. Cancer Res. 69:9003.2009
[Non-Patent Literature 6] Chapuis et al, Sci Transl Med. 5:174ra27.2013
[Non-Patent Literature 7] Blood.116: 5045.2010
[Non-Patent Literature 8] Ito et al. Lancet.331:413. 1988
[Non-Patent Literature 9] CYRANOSKI. Nature. vol.488. 139.2012
[Non-Patent Literature 10] Takahashi and Yamanaka.Cell. 126:663-673.2006
[Non-Patent Literature 11] Takahashi et al. Cell.131: 861-872.2007
[Non-Patent Literature 12] Grskovic et al. Nat.Rev.Drug. Dscov. 10,915-929(2011)
[Non-Patent Literature 13] Morgan R. A. et al, Science, 314:126.2006
[Non-Patent Literature 14] Timmermans et al.Journal of Immunology. 182: 6879-6888.2009
[Non-Patent Literature 15] Blood. 111:1318.2008
[Non-Patent Literature 16] Nature Immunology.11: 585.2010

The prior art documents listed above are herein incorporated by reference.

SUMMARY OF INVENTION

An object of the present application is to provide a cell based immunotherapy that is more efficient and safer than conventional immunotherapies.

According to the present application, a cell-based immunotherapy method which comprises inducing T cell progenitors or mature T cells from pluripotent stem cells bearing genes encoding a TCR specific for a desired antigen, and allogenically administering the obtained T cell progenitors or mature T cells to a patient having HLAs that match the HLAs of the donor from which the pluripotent stem cells were established to a predetermined extent.

In the method of the present application, the pluripotent stem cells bearing genes encoding a T cell receptor specific for a desired antigen may be obtained by introducing genes encoding the antigen specific T cell receptor into the pluripotent stem cells.

The T cells used in the cell-based immunotherapy are a clonally expanded T cell population and therefore, all of the cells in the population bear a single TCR. Accordingly, the possibility of causing a graft-versus-host reaction is significantly low and the cells can be used not only for autologous transplantation hut also for allogenic transplantation. The art could not expect the method provided herein in view of the commonsense that "allogenic transplantation of T cells is an absolute contraindication".

EFFECT OF THE INVENTION

According to the present application, the inventors could unexpectedly solve the above recognized problems to some extent. The following advantages are available:

1) No need for preparing T cells for transplantation for each patient. Therefore, preparation for the cell-based immunotherapy can be conducted previously.

2) The safety and quality of the cells to be transplanted can be verified before the treatment.

3) Even if an allograft between the HLA-match patient and donor, some minor antigens do not match and therefore, the transplanted cells are eventually rejected by the patient's immune reaction. A safe treatment with significantly less risk of canceration of the transplanted cells can be conducted.

Further, in view of the fact that the T cells for transplantation of the present application may be obtained by a method having a step of introducing genes encoding a desired antigen specific T cell receptor (TCR) into the pluripotent stem cells, the following advantages are also expected:

1) By introducing genes encoding a TCR whose efficacy and safety have previously been confirmed, the quality of the T cells for transplantation can be guaranteed;

2) TCR gene insertion site can be identified and a safe clone can be confirmed beforehand. Then, the problem of carcinogenesis of transplanted cells can be avoided.

3) Upon re-differentiating pluripotent stem cells in which genes encoding TCR were introduced into T cells, the introduced TCR will express prior to the TCR of the original pluripotent stem cells (endogenous TCR) and therefore, the endogenous TCR chains will not be rearranged and unintended reaction may not occur.

DETAILED DESCRIPTION OF PREFERRED EMBODIMENTS

In the specification and claims, "pluripotent stem cells" refer to stem cells having pluripotency, i.e. an ability to differentiate into many types of cells in the body, and self-propagation ability. Examples of pluripotent stem cells may include embryonic stem cells (ES cells), nuclear transfer embryonic stem cells (ntES cells), germline stem cells (GS cells), embryonic germ cells (EG cells), induced pluripotent stem cells (iPS cells), cultured fibroblasts and pluripotent cells derived from myeloid stem cells (Muse cells). For creating a cell bank for the cell-based immunotherapy from human donors having specific HLAs, iPS cells are preferably used. In the specification and claims, iPS cells obtained by introducing a TCR are called as "TCR-iPS cells"

The iPS cells may be those established from any somatic cells.

The procedures for inducing iPS cells from a somatic cell have been known to the art. iPS cells can be established by introducing the Yamanaka factors into a somatic cell. (Takahashi and Yamanaka. Cell. 126:663-673.2006, Takahashi et al. Cell. 131:861-872.2007 and Grskovic et al. Nat.Rev.Drug Dscov.10:915-929.2011) The reprogramming factors used for inducing iPS cells are not limited to the Yamanaka factors and any of reprogramming factors or procedures that have been known to the art may be employed.

Genes encoding various antigen specific T cell receptors clinically used in the T cell therapy described in background art "B" have been known to the art and have been confirmed to be safe. For example, genes encoding for a TCR specific for a WT1 antigen have been known. Genes encoding a TCR may be those known to the art as well as TCR genes to be identified from now on. Genes encoding a TCR may also be isolated from T cells with the desired antigen specificity isolated or induced from a patient suffered from a cancer or an infectious disease. According to the method of the present application, the site to which the genes are introduced can be identified and the safety of the clone to be used for the therapy can be verified before use. Therefore, the risk of carcinogenesis can be avoided.

In the method of the present application, TCR genes may be introduced into iPS cells. The procedure for introducing the TCR genes into iPS cells may be any of those known to the art and may be conducted as taught by Morgan R. A. et al. Science. 314:126.2006. In particular, a suitable vector bearing the TCR genes may be introduced into the iPS cells. For example, TCR genes may be introduced by a vector such as virus, plasmid and artificial chromosome vectors; or by means of lipofection, liposome or microinjection. Examples of the virus vectors include retrovirus vectors, lentivirus vectors, adenovirus vectors, adeno-associated virus vectors and Sendai virus vectors. Examples of the artificial chromosome vector include human artificial chromosome (HAG), yeast artificial chromosome (YAC), and bacterial artificial chromosome (BAC and PAC). Examples of the plasmid which may be used include plasmids for mammalian cells. The vector may contain a regulatory sequence(s) such as a promoter, enhancer, ribosome binding sequence, terminator and/or polyadenylation site to enable expression of the TCR genes. If desired, the vector may also contain a selection marker such as a drug resistance gene (e.g., kanamycin-resistant gene, ampicillin-resistant gene or puromycin-resistant gene), thymidine kinase gene or diphtheria toxin gene; and a reporter such as the green-fluorescent protein (GFP), β-glucuronidase (GUS) or FLAG.

As above described, when genes encoding a TCR are introduced into iPS cells by using a vector, the TCR genes are introduced into the site on the genome other than the site encoding the endogenous TCR. Alternatively, the TCR locus on the genome may be replaced with the genes encoding the desired TCR. For introducing the genes encoding a TCR with a vector, the iPS cells may preferably be those induced from a somatic cell other than T cells. Alternatively, iPS cells established from a T cell are preferable when the TCR genes are introduced by means of "replacement". For example, the already re-arranged TCRα and TCR genes may be replaced with the desired TCRα and TCR genes by means of genome editing. Advantages of this procedure may include 1) the timing and level of expression of the introduced TCR can be adjusted so that they are similar to the endogenous TCR, and therefore, high quality T cells can be generated, and 2) TCR can be introduced without giving damages to the genome.

TCR-iPS cells, which may be obtained by introducing genes encoding a TCR into iPS cells, are then differentiated into T cell progenitors or mature T cells. The procedure for differentiating pluripotent stem cells into T cells may be that taught by Timmermans et al. Journal of Immunology. 182: 6879-6888.2009.

In the specification and claims, "T cell progenitors" may cover cells at any stage of the T cell development, from undifferentiated cells corresponding to hematopoietic stem cells to the cells at the stage just before the cells undergo positive selection/negative selection. Details of the differentiation of T cells are explained in Blood. 111:1318.2008 and Nature Immunology. 11: 585.2010.

In the T cell progenitors or mature T cells re-differentiated from the TCR-iPS cells, the introduced TCR will be expressed without expressing endogenous TCR. Therefore, unintended reaction may not occur and a safe therapy can be provided.

In another embodiment, Rag1 and/or Rag2 gene in the iPS cells may be knocked out to completely avoid re-arrangement of the endogenous TCR. Safer treatments can be provided by employing thus produced cells. It will be enough to knock out one of Rag1 and Rag 2 genes. Further, siRNA that suppress the expression of the endogenous TCR may be introduced simultaneously.

The cell-based immunotherapy provided by the present application may be used for the treatment of diseases relating to the antigen to which the introduced TCR specifically binds. Examples may include cancers, infectious diseases, autoimmune diseases and allergic diseases. In the method of the present application, the re-generated T cells are dispersed in a suitable media such as saline or PBS and the dispersion may be administered to a patient having a certain matching level of the HLA to the donor of the cells from which the pluripotent stem cells were established. The matching level of the donor and the patient may be complete match. When the donor is homozygous for HLA haplotype (hereinafter referred to as "HLA haplotype homo") and the patient is heterozygous for HLA haplotypes (hereinafter referred to as "HLA haplotype hetero"), one of the patient's HLA haplotypes should match the donor's homozygous HLA haplotype. The cells may be administered intravenously.

For example, iPS cells may be those having an HLA haplotype that matches at least one of the HLA haplotypes of the subject to be treated and selected from an iPS cell bank in which iPS cells established from cells of donors with a homozygous HLA haplotype are stored in connection with information regarding HLA of each donor.

The number of the cells to be administered is not limited and may be determined based on, for example, the age, sex, height and body weight of the patient and disease and conditions to be treated. The optimal cell number may be determined through clinical studies.

T cells may target various antigens and therefore, the method of this application may be applied for a cell-based immunotherapy against various diseases including cancers, infectious diseases, autoimmune diseases and allergic diseases. For example, a high proportion of hematopoietic organ tumors such as leukemia, myelodysplastic syndrome, multiple myeloma, and malignant lymphoma, as well as solid tumors such as stomach cancer, colon cancer, lung cancer, breast cancer, germ cell cancer, liver cancer, skin cancer, bladder cancer, prostate cancer, uterine cancer, cervical cancer and ovarian cancer express the WT1 gene. Accordingly, when TCR-iPS cells are produced by introducing TCR genes specific for a WT1 antigen into iPS cells and CTL cells are re-generated from the TCR-iPS cells, the CTL cells are effective for the cell-based immunotherapy for WT1 gene expressing cancers.

In various proposed therapies wherein various cells or tissues, other than T cells, that are differentiated from iPS cells are transplanted, the cells to be transplanted are expected to be fixed in the body of the patient for his/her entire life. In regenerative therapies that use cells or tissues regenerated from iPS cell stock for allogenic transplantation, the patients need to take immune suppressing drugs for their entire life. This is disadvantageous point compared to the autologous transplantation. On the other hand, T cells regenerated from TCR-iPS cells according to the present application, the allogenically transplanted T cells are eventually rejected after a certain period. That is, allogenic graft will be eventually rejected based on mismatches in minor histocompatibility antigens even in the HLA-matched donor and recipient. In this point, the cell-based immunotherapy provided by this application is advantageous than the other allogenic transplantation of the cells or tissues regenerated from iPS cells.

Further, the present method does not require the preparation of the cells for each patient. Previously prepared TCR-iPS cells having the desired antigen specificity, or T cell progenitors or mature T cells regenerated from the TCR-iPS cells may be stocked and used. Accordingly, this method has advantages not only of shortening the period for preparation of the cell-based immunotherapy but also enabling the verification of the quality of the cells before transplantation.

For example, T cell preparation targeting for a cancer antigen may be provided. Genes encoding a TCR that had previously been verified to be effective and safe in the TCR gene therapy for the cancer are introduced into, for example, iPS cells established from a donor with a homozygous HLA haplotype. An iPS cell bank may be created with those TCR-iPS cells. For the treatment of a patient having heterozygous HLA haplotype suffered from a cancer expressing an antigen that will be recognized by the introduced TCR, T cells may be re-differentiated from TCR-iPS cells selected from the TCR-iPS cell bank and administered allogenically to the patient. T cell progenitors or T cells may previously re-generated from the TCR-iPS cells and cryopreserved in order to provide more quick treatment.

Examples of TCR genes that can be used in the method of this application may include genes encoding a WT1 antigen specific TCR cloned from the TAK-1 cells by Prof. Masaki YASUKAWA of Ehime University (Blood.95:286.2000; Blood.118:1495.2011). iPS cells may be those obtained from those stored under the iPS cell stock project by the Center for iPS cell Research and Application. An iPS cell line HPS0077 deposited with RIKEN BioResource Center (RIKEN BRC) may be used as iPS cells having an HLA haplotype most frequent in Japan in homozygous.

The application will be explained in more detail with the examples shown below.

EXAMPLE 1

Establishment of iPS Cells Into Which a Class I Restricted WT1 Antigen Specific TCR is Introduced The original iPS cells used here were LMP2-T-iPS cells (clone LMP2 #1) prepared in Department of Immunology, Institute for. Frontier Medicinal Sciences, Kyoto University, Kyoto, Japan.

HLA-A2402 restricted WT1 specific TCR used here was obtained from a clone B10, which was cloned in Laboratory of immunology and hematopoiesis, Department of Immunology, Graduate School of Medicine, Osaka University, Suita-shi, Osaka, Japan (Anticancer Research. 32(12):5201-5209.2012). The TCR recognizes the peptide having amino acid sequence CMTWNQMNL (SEQ ID NO: 4) in the HLA-A2402-resteicted manner.

1) Cloning of WT1 Specific TCR Genes by Means of the Rapid Amplification of cDNA Ends (RACE)

Figure 1:
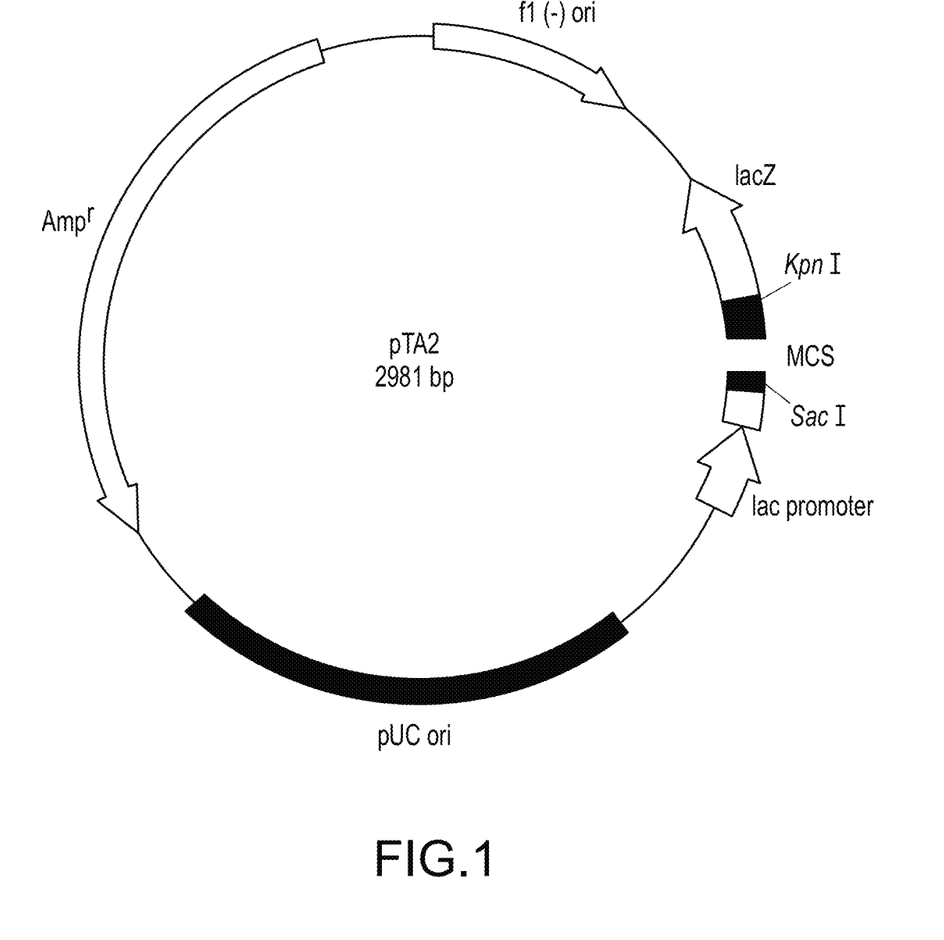
FIG. 1 shows pTA2 vector used in Example 1.

A WT1 specific CTL clone or a CTL clone induced from WT1-T-iPS cell was amplified and RNAs of the cells were obtained. Full length cDNA was obtained by using SMARTer RACE cDNA amplification kit (Clontech Laboratories, Inc.) and was used as a template. TCR genes were amplified by using a primer targeting the 3'-end of the TCRα chain: CACAGGCTGTCTTACAATCTTGCAGATC (SEQ ID NO: 1) or 3'-end of the TCR chain: CTCCACTTCCAGGGCTGCCTTCA (SEQ ID NO: 2) or TGACCTGGGATGGTTTTGGAGCTA (SEQ ID NO: 3) to obtain double stranded WT1-TCR cDNA, Thus obtained double stranded cDNA was inserted into pTA2 vector (TOYOBO, see FIG. 1) and introduced into a cell line. The properties including specificity of the WT1 TCR were evaluated using the transfected cells.

2) Preparation of Lentiviral Vector Incorporated with WT1-TCR

Figure 2:
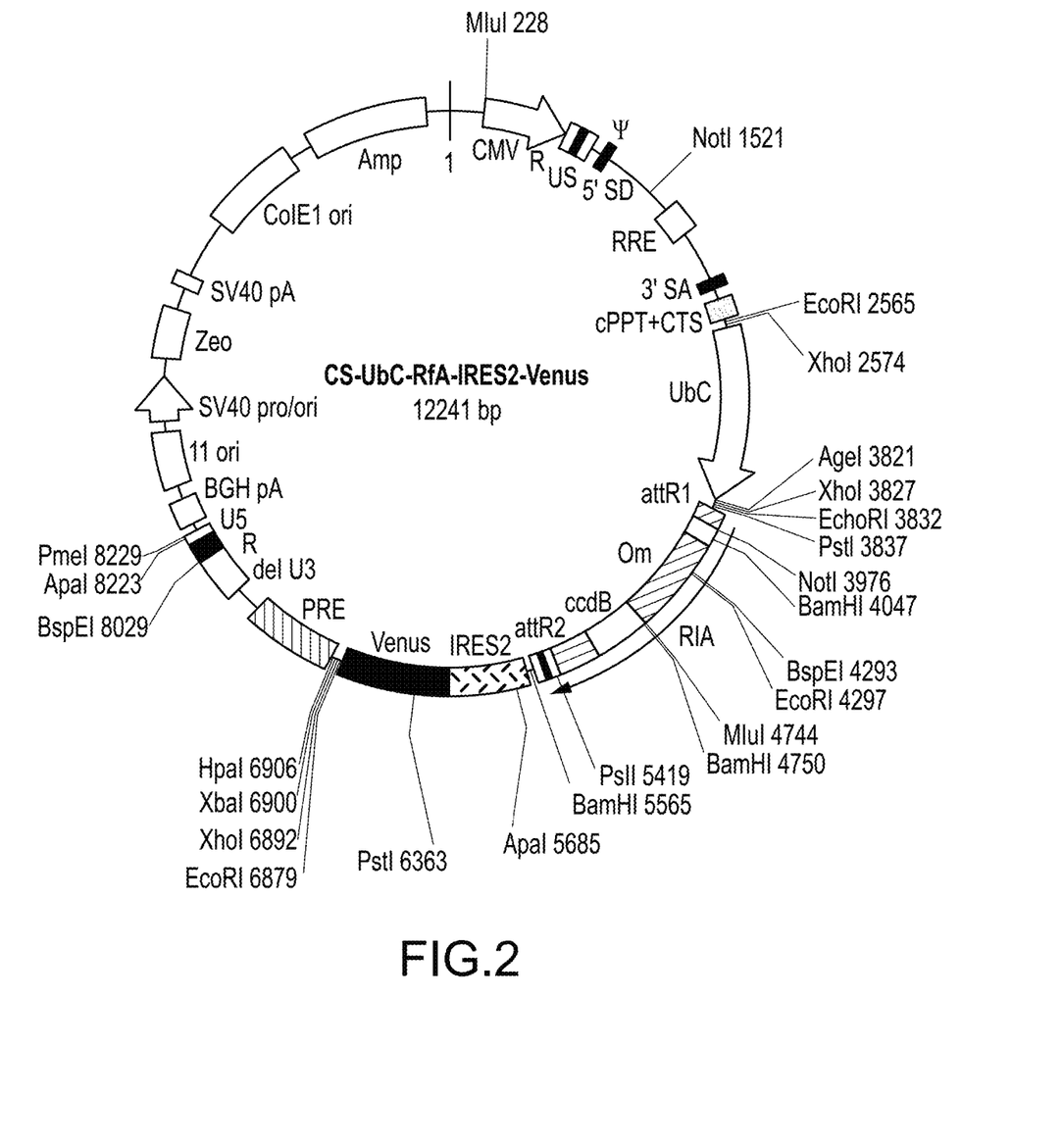
FIG. 2 shows Lentiviral vector used in Example 1.

CS-UbC-RfA-IRES2-Venus vector (FIG. 2) was obtained from Subteam for Manipulation of Cell Fate, RIKEN BioResource Center, Tsukuba, Ibaraki, Japan. WT-TCR gene was incorporated in the vector with the Gateway system to give CS-UbC-RfA-IRES2-Venus/WT1-TCR.

3) Preparation for Supernatant of WT1-TCR Introduced Lentivirus

CS-UbC-RfA-IRES2-Venus/WT1-TCR was introduced into LentiX-293T packaging cells with X-treamGENE9 (Roche). The medium was exchanged on the next day and on day 2, the culture supernatant was collected and used as lentiviral supernatant.

4) Establishment of WT1-TCR Transduced T-iPS Cells

LMP2-T-iPS cells were treated with TrypLE Select (Life Technologies) to give completely single-cell suspension. The suspension was centrifuged and the pellet was dispersed by the lentiviral supernatant, and then, the obtained suspension was centrifuged at 3000 rpm at 32° C. for one hour so that lentivirus infects and then, WT1-TCR was introduced into the LMP2-T-iPS cells.

After the infection, the cells were suspended in the medium for iPS cells and seeded on the feeder cells. The LMP2-T-iPS cells in which WT1-TCR was introduced (WT1-TCR/LMP2-T-iPS cells) were fluoroscopically selected on the basis of expression of Venus protein included in the vector.

C. Picking up WT1-TCR/LMP2-T-iPS Cell Colonies from the Culture

1. Two weeks after the introduction of the Yamanaka factors, colonies of iPS cells were visually observed.

2. Colonies were mechanically picked up with a 200 µl pipette tip.

3. Several clones were established individually.

3) Induction of T cells from the iPS Cells.

Media used are as follows:

TABLE 1

Medium A: for maintenance of OP9 stromal cells

| contents | amount added | final conc. |
| --- | --- | --- |
| αMEM medium | 500 mL | |
| FCS | 125 mL | 20% |
| penicillin-streptomycin solution* | 6.25 mL | 1% |
| Total | 631.25 mL | |

*Mixture of Penicillin 10,000 U/ml) and Streptomycin (10,000 µg/ml). The final concentrations were 100 U/ml and 100 µg/ml, respectively.

TABLE 2

Medium B: for inducing differentiation of T cells

| contents | amount added | final conc. |
| --- | --- | --- |
| αMEM medium | 500 mL | |
| FCS | 125 mL | 20% |
| penicillin-streptomycin solution* | 5 mL | 1% |
| hrIL-7 (stock: 10 µg/mL) | 315 µL | 5 ng/mL |
| hrFIT-3L (stock: 10 µ/mL) | 315 µL | 5 ng/mL |
| hrSCF (stock: 10 µg/mL) | 630 µL | 10 ng/mL |
| Total | 631.26 mL | |

*Mixture of Penicillin (10,000 U/ml) and Streptomycin (10,000 µg/ml). The final concentrations were 100 U/ml and 100 µg/ml, respectively.

TABLE 3

Medium C: for inducing from immature T cells into mature T cells

| contents | amount added | final conc. |
| --- | --- | --- |
| αMEM medium | 500 mL | |
| FCS | 125 mL | 20% |
| penicillin-streptomycin solution* | 5 mL | 1% |
| hrIL-7 (stock: 10 µg/mL) | 315 µL | 5 ng/mL |
| Total | 630.315 mL | |

*Mixture of Penicillin (10,000 U/ml) and Streptomycin (10,000 µg/ml). The final concentrations were 100 U/ml and 100 µg/ml, respectively.

A. Preparation of OP9 Cells

Six milliliters (6 mL) of 0.1% gelatin solution in PBS was added to a 10 cm dish (Falcon) and incubated for 30 minutes at 37° C. The gelatin solution was then removed and 10 ml of medium A was added to the dish. OP9 stromal cells were obtained from a confluent culture and seeded in the dish. Four days after, medium A 10 mL was added to the dish (final amount was 20 mL).

B. Induction of Hematopoietic Progenitor Cells from iPS Cells

The medium in the OP9 stromal cell culture to be used for the co-culture was aspirated and replaced with fresh medium A. The medium in the human iPS cell culture dish was also aspirated and 10 ml of fresh medium A was added. The iPS cell mass was cut with an EZ-passage roller. The cut iPS cell mass was suspended by using a pipetman with a 200 µl tip. The number of the iPS cell clusters was visually counted and approximately 600 iPS cell clusters were seeded on the OP 9 cells. Three or more dishes per clone of human iPS cells were used, and when subculturing, the cells in all dishes were once pooled in one dish and then redistributed to the same number of dishes to reduce the disparity between the dishes.

Day 1: (the medium was replaced)

Whether the iPS cell mass adhered to the dish and started to differentiate were confirmed. The cell culture medium was replaced with 20 mL of fresh medium A.

Day 5: (a half of the medium was replaced)

A half of the cell culture medium was replaced with 10 mL of fresh medium A.

Day 9: (a half of the medium was replaced)

A half of the cell culture medium was replaced with 10 mL of fresh medium A.

Day 13: (Induced mesodermal cells were transferred from OP9 cell layer onto OP9/DLL1 cell layer)

Cell culture medium was aspirated to remove and the surface of the cultured cells were washed with HBSS(+Mg+

Ca) to washout the cell culture medium. 10 mL of Collagenase IV 250U in HBSS (+Mg+Ca) solution was added to the dish and incubated for 45 minutes at 37° C.

The collagenase solution was removed by aspiration and the cells were washed with 10 mL of PBS(−). Then, 0.05% trypsin/EDTA solution was added to the dish and the dish was incubated for 20 minutes at 37° C. After the incubation, the sheet like cell aggregates peeled from the bottom of the dish and the cell aggregates were mechanically fragmented to smaller sizes by means of pipetting. Thus treated cells were added with fresh medium A 20 mL and cultured for more 45 minutes at 37° C.

The culture medium containing the floating cells was passed through a 100 μm mesh and the cells were collected. The cells were then centrifuged at 1200rpm for 7 minutes at 4° C. The obtained pellet was suspended in 10 mL of medium B. One-tenth of the suspension was separated and used for the FACS analysis. The remaining cell suspension was seeded to new dishes containing OP9/DLL1 cells. Cell suspensions obtained from several dishes were pooled and the pooled cells were seeded to the same number of new dishes.

In order to ascertain whether or not hematopoietic progenitor cells were contained in the obtained cells, FACS analysis was carried out using anti-CD34 antibody and anti-CD43 antibody. When a sufficient number of cells could be confirmed in the CD34lowCD43+ cell fraction, it was determined that hematopoietic progenitor cells were induced.

C. Induction of T Cells from Hematopoietic Progenitor Cells.

Then, the obtained cells were seeded on OP9/DLL1 cells. In this step, cell sorting of the $CD34^{low}CD43^+$ cell fraction was not performed. When this fraction is sorted, the efficiency of differentiation of T cells could be reduced in comparison with the case where sorting is not performed due to the decrease of the cells or damage to the cells by sorting.

During the culturing period, FACS analysis was conducted several times to confirm the differentiation stages. A considerable number of dead cells were observed over the culturing period. Before the FACS analysis, dead cells were preferably eliminated by using, for example, Propidium Iodide (PI) or 7-AAD.

Day 16: (Cells were subcultured)

The cells loosely adhered to the OP9/DLL1 cells were gently dissociated by pipetting several times. The cells were passed through a 100 μm mesh and collected in a 50 mL conical tube. The tube was centrifuged at 1200 rpm for 7 minutes at 4° C. The pellet was dispersed in 10 mL of medium B. Thus prepared cells were seeded on the OP9/DLL1 cells.

Day 23: (Cells were subcultured) Blood cell colonies began to appear.

The cells loosely adhered to the OP9/DLL1 cells were gently dissociated by pipetting several times. The cells were passed through a 100 μm mesh and collected in a 50 mL conical tube. The tube was centrifuged at 1200 rpm for 7 minutes at 4° C. The pellet was dispersed in 10 mL of medium B. Thus prepared cells were seeded on the OP9/DLL1 cells.

Day 30: (Cells were subcultured)

The cells loosely adhered to the OP9/DLL1 cells were gently dissociated by pipetting several times. The cells were passed through a 100 μm mesh and collected in a 50 mL conical tube. The tube was centrifuged at 1200 rpm for 7 minutes at 4° C. The pellet was dispersed in 10 mL of medium B. Thus prepared cells were seeded on the OP9/DLL1 cells.

Day 37: Cells were subcultured

The cells loosely adhered to the OP9/DLL1 cells were gently dissociated by pipetting several times. The cells were passed through a 100 μm mesh and collected in a 50 mL conical tube. The tube was centrifuged at 1200 rpm for 7 minutes at 4° C. The pellet was dispersed in 10 mL of medium B. Thus prepared cells were seeded on the OP9/DLL1 cells.

Day 44: $CD4^+CD8^+$ T cells were confirmed and started to inducing into CD8 SP cells In order to confirm T cells were duly induced, the cells on Day 44 were analyzed by FACS with anti CD4 antibody and anti CD8 antibody. The generation of CD4+CD8+ cells was confirmed. Then, anti-CD3/28 antibody and huIL-2 were added to the cells. The T cells containing the CD4+CD8+ cells were seeded on the fresh OP9/DLL1 cell layer in each well of a 24-well plate at a density of $3\times10^5$ cells/well. Anti-CD3 antibody (50 ng/mL), anti-CD28 antibody (2 ng/mL) and huIL-2 (200 U/mL) were added together to each well.

Day 50: $CD4^-CD8^+$ cells were observed

Figure 3:
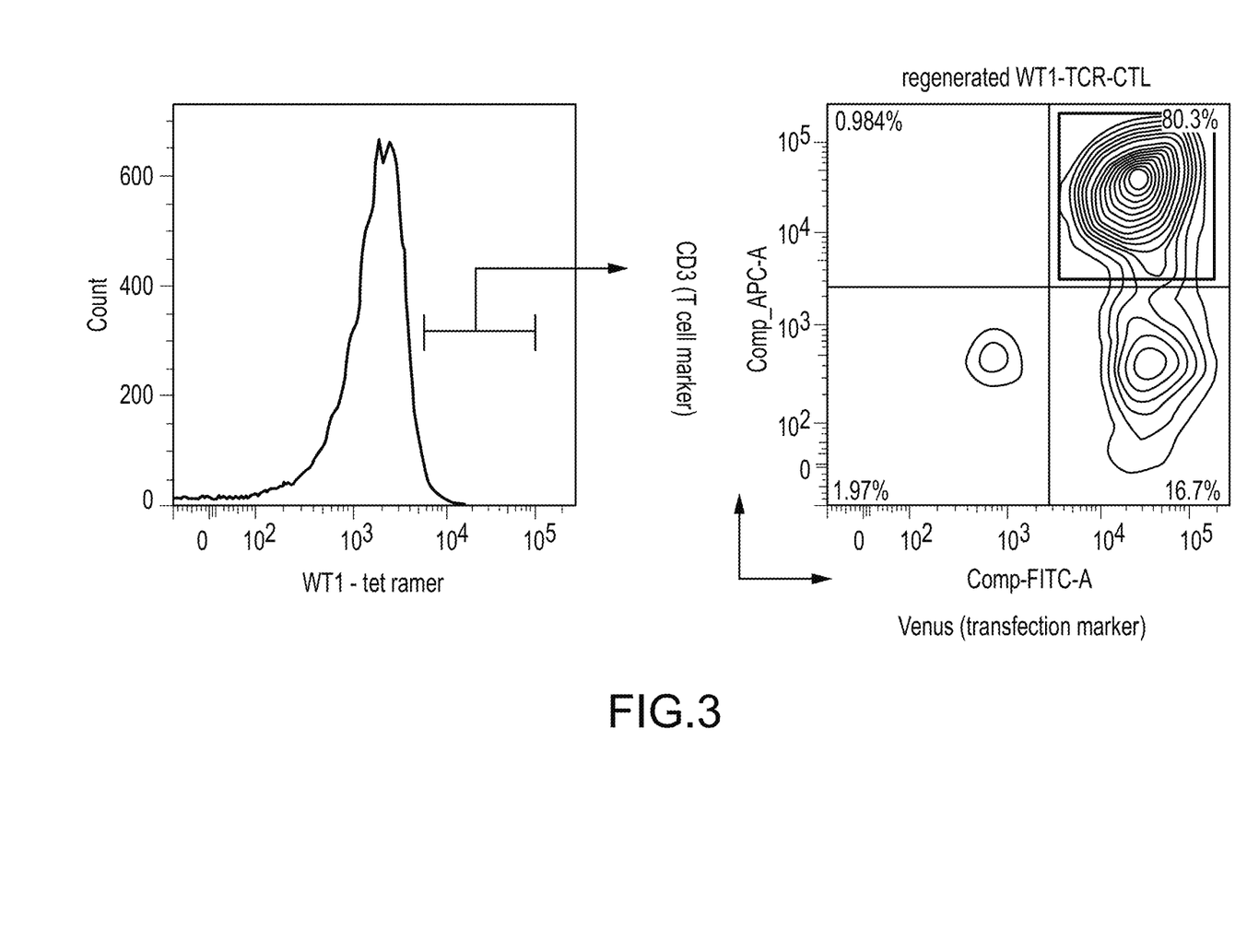
FIG. 3 shows that mature T cells bearing the WT1-TCR that were introduced into the iPS cells to give the TCR-iPS cells were re-generated from the TCR-iPS cells in Example 1.

On day 6 of the addition of anti-CD3 antibody, mature CD8 single positive cells were generated. The generated cells were stained with WT1-tetramer and anti-CD3 antibody (FIG. 3). The generation of T cells expressing the introduced WT1-TCR was confirmed.

EXAMPLE 2

Establishment of iPS Cells with a Homozygous HLA into Which a Class I Restricted WT1 Antigen Specific TCR is Introduced The original iPS cells were established from peripheral blood mononuclear cells of a healthy donor in Department of Immunology, Institute for Frontier Medicinal Sciences, Kyoto University, Kyoto, Japan. The iPS cell clone has a homozygous HLA haplotype of HLA-A*33:03; B*44:03; C*140:3; DRB1*1302.

HLA-A0201 restricted WT1 specific TCR was derived from Opt3E2, which was cloned in Laboratory of immunology and hematopoiesis, Department of Immunology, Graduate School of Medicine, Osaka University, Suita-shi, Osaka, Japan. The TCR recognizes the peptide having amino acid sequence RMFPNAPYL (SEQ ID NO: 5).

Preparation of the vector and transfection thereof into iPS cells were performed as described in Example 1.

Figure 4:
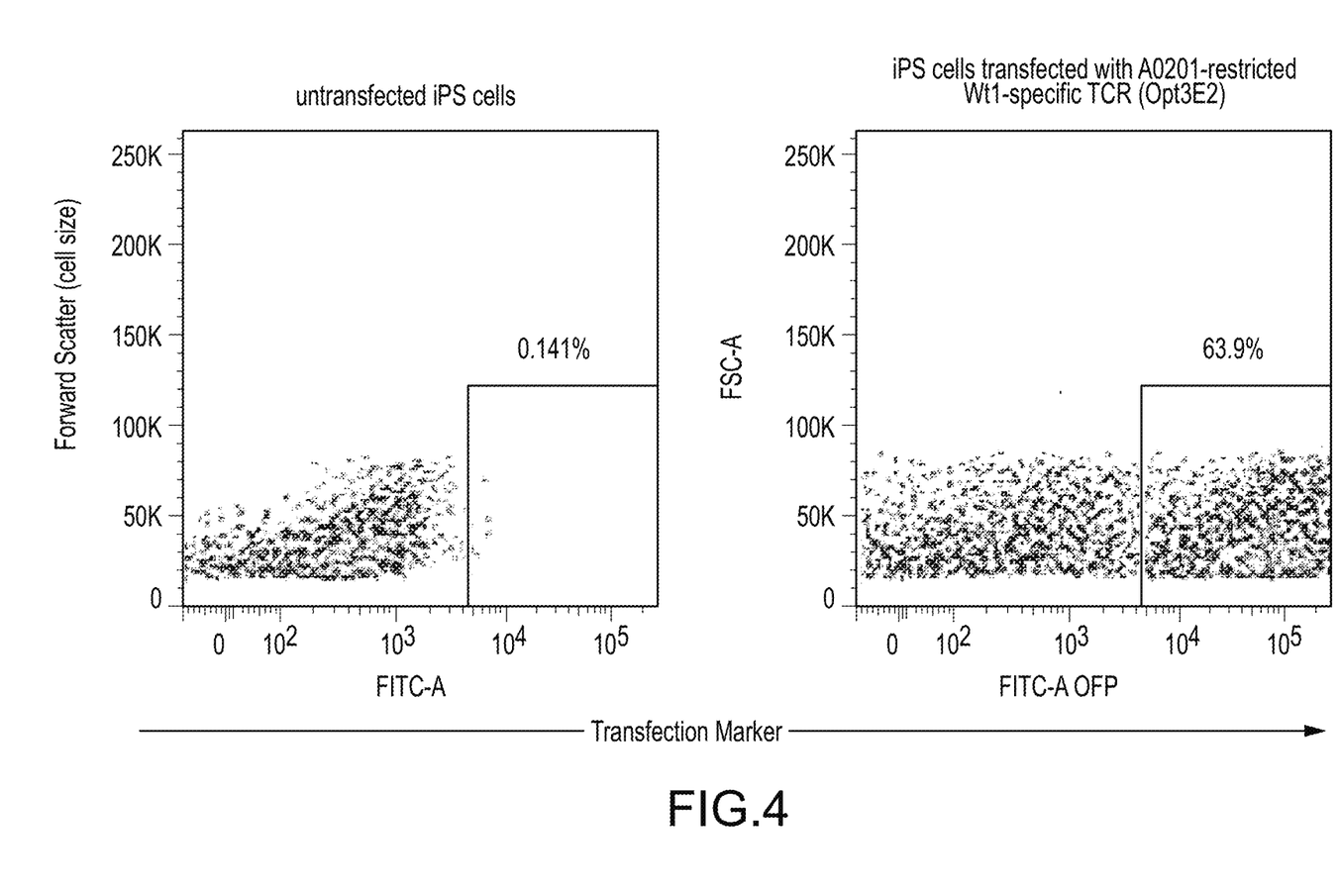
FIG. 4 shows that iPS cells that were introduced with genes encoding a TCR specific for HLA-A0201-restricted WT1 were obtained in Example 2.

1. A single-cell suspension of the iPS cells transfected with the genes was analyzed by flow cytometry. It was confirmed that genes encoding HLA-A0201-restricted WT1 specific TCR were efficiently introduced in the iPS cells (FIG. 4).

Figure 5:
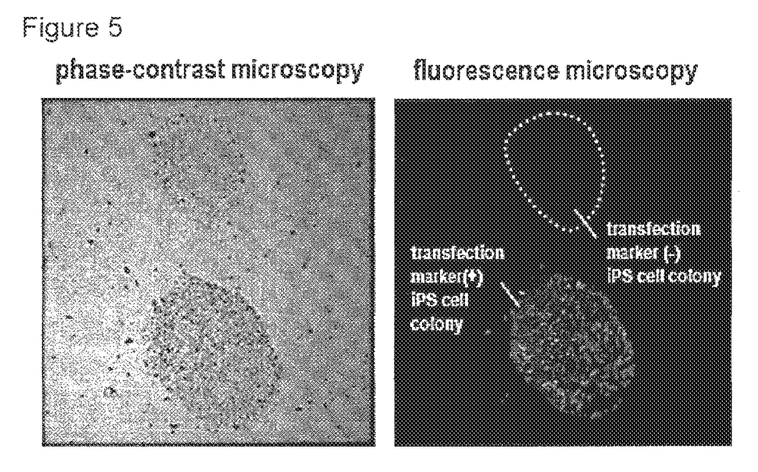
FIG. 5 shows that a clone of the iPS cells that were introduced with genes encoding a TCR specific for HLA-A0201-restricted WT1 was obtained in Example 2.

2. The iPS cells transfected with the TCR genes were seeded on the dish and clonally expanded. FIG. 5 shows colonies of the iPS cells after one week culture. The colonies of the iPS cells into which the genes were introduced were confirmed as fluorescent positive colonies. FIG. 5 confirms that an iPS cell clone to which genes encoding HLA-A0201 restricted WT1 specific TCR was obtained. Then, the positive colony was picked up.

EXAMPLE 3

Establishment of iPS Cells with a Homozygous HLA into Which a Class II Restricted WT1 Antigen Specific TCR is Introduced The original iPS cells were established from peripheral blood mononuclear cells of a healthy donor in Department of Immunology, Institute for Frontier Medicinal Sciences, Kyoto University, Kyoto, Japan in the same procedure in Example 2. The iPS cell line has a homozygous HLA.

The class II restricted WT1 specific TCR genes were derived from Clone K and Clone 10, which were cloned in Laboratory of immunology and hematopoiesis, Department of Immunology, Graduate School of Medicine, Osaka University, Suita-shi, Osaka, Japan. Clone K and Clone 10 are restricted to HLA-DRB1*0405 and HLA-DPB1*0501, respectively, and recognize the peptide sequence WT1-332 (KRYFKLSHLQMHSRKH(SEQ ID NO: 6)) (Microbiol Immunol 52: 591-600, 2008).

Preparation of the vector and transfection thereof into iPS cells were performed in the same manner as described in Example 1.

Figure 6:
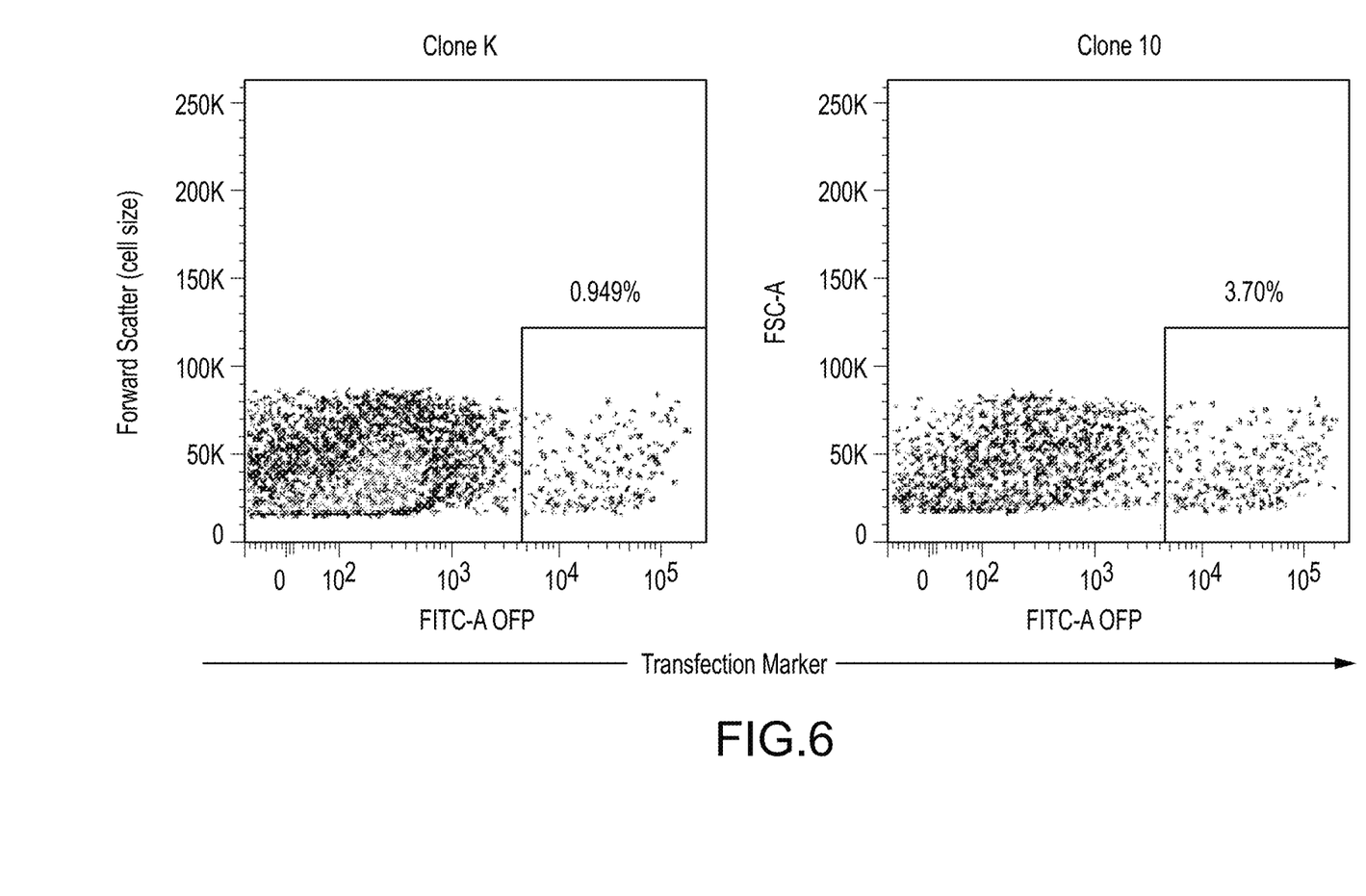
FIG. 6 shows that genes encoding a TCR specific for WT1 were duly introduced in the iPS cells in Example 3.

1. A single-cell suspension of the iPS cells transfected with the genes was analyzed by flow cytometry. The results are shown in FIG. 6. It was confirmed that WT1 specific TCR genes derived from Clone 10 and Clone K were duly introduced in the iPS cells.

EXAMPLE 4

Establishment of iPS Cells with a Homozygous HLA into Which a Class I Restricted WT1 Antigen Specific TCR is Introduced The original iPS cells were established from peripheral blood mononuclear cells of a healthy donor in Department of Immunology, Institute for Frontier Medicinal Sciences, Kyoto University, Kyoto, Japan in the same manner as described in Example 2. The iPS cell line has homozygous HLA.

Class I restricted WT1 specific TCR genes were cloned from Clone WT1#9 and Clone WT1#3-3 in Department of Immunology, Institute for Frontier Medicinal Sciences, Kyoto University, Kyoto, Japan.

Preparation of the vector and transfection thereof into iPS cells were performed in the same manner as described in Example 1.

Figure 7:
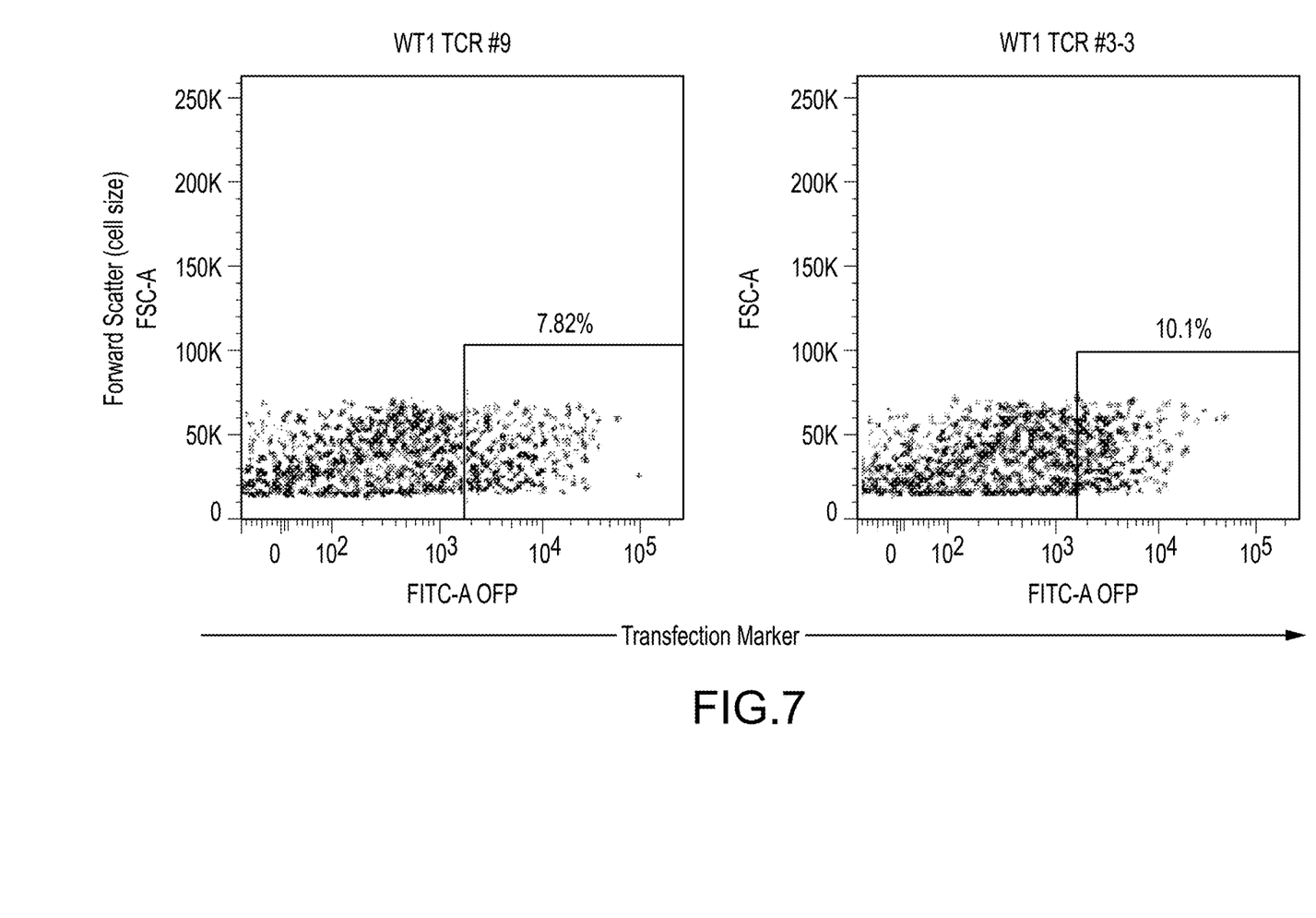
FIG. 7 shows that genes encoding a TCR specific for WT1 were duly introduced in the iPS cells in Example 4.

2. A single-cell suspension of the iPS cells transfected with the genes was analyzed by flow cytometry. The results are shown in FIG. 7. It was confirmed that WT1 specific TCR genes derived from Clone #9 and Clone #3-3 were duly introduced in the iPS cells.

---

What is claimed is:

1. An in vitro method for inducing T cells expressing a single T cell receptor for a cell-based immunotherapy, comprising the steps of:
    (1) providing human induced pluripotent stem (iPS) cells;
    (2) introducing re-arranged genes encoding an antigen specific T cell receptor into the iPS cells; and
    (3) inducing T cells from the iPS cells obtained in step (2), thereby obtaining T cells expressing said antigen specific T cell receptor as the single T cell receptor,
    wherein none of the genes encoding Rag 1 and Rag 2 in the iPS cells is knocked out, and wherein the iPS cells were induced from a somatic cell other than a T cell.

2. The method according to claim 1, wherein the iPS cells were established from a donor with a homozygous HLA haplotype that matches at least one of HLA haplotypes of a subject to be treated.

3. The method according to claim 1, wherein the immunotherapy is for the treatment of a disease involving immunity.

4. The method according to claim 3, wherein the immunotherapy is for the treatment of a cancer.

5. The method according to claim 4, wherein the cancer is a WT1 gene expressing cancer.

6. The method according to claim 3, wherein the disease involving immunity is selected from the group consisting of a cancer, an infectious disease, an autoimmune disease and an allergic disease.

7. The method according to claim 1, wherein the iPS cells in step (1) are established from cells of a healthy donor.

8. The method according to claim 1, wherein the iPS cells in step (1) are established from peripheral blood mononuclear cells of a healthy donor.

* * * * *